United States Patent [19]
Shih et al.

[11] Patent Number: 5,252,611
[45] Date of Patent: * Oct. 12, 1993

[54] CONTROLLED RELEASE TABLETS INCLUDING STRONGLY SWELLABLE, MODERATELY CROSSLINKED POLYVINYLPYRROLIDONE

[75] Inventors: Jenn S. Shih, Paramus; Jui-Chang Chuang, Wayne; Rama K. Haldar, Randolph, all of N.J.

[73] Assignee: ISP Investments Inc., Wilmington, Del.

[*] Notice: The portion of the term of this patent subsequent to Dec. 17, 2008 has been disclaimed.

[21] Appl. No.: 915,500

[22] Filed: Jul. 20, 1992

[51] Int. Cl.$^5$ ............ C08F 2/18; A61K 47/32
[52] U.S. Cl. ............ 514/772.5; 526/238.23; 526/261; 526/264
[58] Field of Search ......... 514/772.5, 772.3; 526/264, 261, 238.23

[56] References Cited

U.S. PATENT DOCUMENTS

| | | | |
|---|---|---|---|
| 3,878,175 | 4/1975 | Steckler | 526/264 |
| 4,036,814 | 7/1977 | Howes et al. | 526/264 |
| 4,361,689 | 11/1982 | Patel et al. | 526/264 |
| 4,873,299 | 10/1989 | Nowakowsky | 526/264 |
| 5,073,614 | 12/1991 | Shih et al. | 526/264 |
| 5,130,388 | 7/1992 | Shih | 526/264 |
| 5,139,770 | 8/1992 | Shih et al. | 526/264 |

FOREIGN PATENT DOCUMENTS

| | | | |
|---|---|---|---|
| 0190996 | 8/1986 | European Pat. Off. | 514/772.5 |
| WO9012041 | 10/1990 | PCT Int'l Appl. | 526/264 |
| 2153678 | 8/1985 | United Kingdom | 514/772.5 |

*Primary Examiner*—Peter F. Kulkosky
*Attorney, Agent, or Firm*—Walter Katz; Marilyn J. Maue; Joshua J. Ward

[57] ABSTRACT

What is described herein is a controlled release, drug-delivery composition which comprises a strongly swellable, moderately crosslinked polyvinylpyrrolidone polymer in the form of fine white powders having a defined aqueous gel volume and Brookfield viscosity which is prepared by precipitation polymerization in the presence of a prescribed amount of crosslinking agent, and an effective amount of a pharmaceutical medicament.

2 Claims, 1 Drawing Sheet

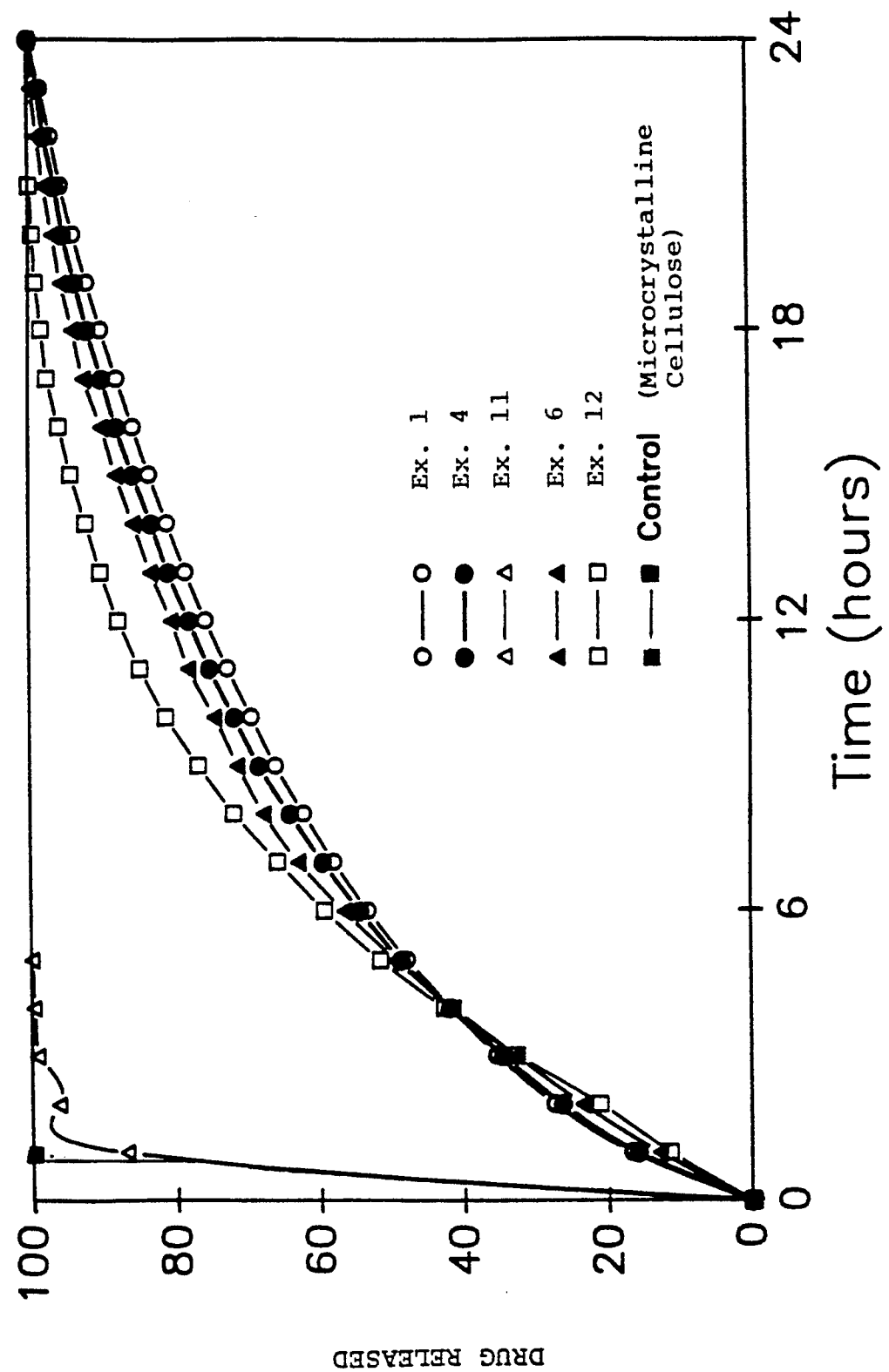

CONTROLLED RELEASE TABLETS INCLUDING STRONGLY SWELLABLE, MODERATELY CROSSLINKED POLYVINYLPYRROLIDONE

BACKGROUND OF THE INVENTION

1. Field of the Invention

In the pharmaceutical industry much work has been devoted during recent years to improving the effectiveness, safety and practicality of orally administered drugs. This invention is specifically directed toward the goal of prolonging the release of an orally taken drug over a period of several hours. Such a prolonged release has the following advantages: peak blood levels of the drug, which sometimes represent toxic levels, are avoided since not all the drug is released into the stomach at the same time; secondly, drug concentrations in the blood are maintained for a longer time within the therapeutic range, thereby increasing the overall effectiveness of the drug and reducing the overall dose-size necessary for treatment; thirdly, drugs which would have to be taken in conventional form several times daily for the treatment of chronic diseases, can be administered in once or twice-a-day dose forms, which are safer and more convenient for the patient.

Conventional dose forms of orally taken drugs are tablets or pills in which the drug is compounded with a water soluble gum or polysaccharide which quickly dissolves or disintegrates in the stomach. However, tablet disintegration is fast and poorly reproducible since it is to a large degree a function of physical motion in the stomach. Therefore, polymeric dosage forms were developed in which the drug-release is diffusion-controlled, independent of physical variables other than polymer compositions and morphology. In these dosage forms the polymer is passed through the body without degradation.

Examples of such a monolithic dose form with uniform drug concentrations are described in Australian Patent No. 16202, and in U.S. Pat. No. 3,390,050, wherein hydrophilic polymer beads are synthesized in the presence of a drug. U.S. Pat. No. 4,267,138 describes an oral dose form in which the release of an active ingredient is controlled by a coating surrounding drug containing particles, which are compressed into tablets. The coatings are complicated mixtures of plasticized synthetic polymers and water.

Australian Patent No. 16202 describes the use of a water swellable poly(2-hydroxyethyl methacrylate) or copolymers of 2-hydroxyethyl methacrylate to imbibe drugs from an aqueous solution. The dried polymer-drug composite forms a controlled oral release device. A similar approach, but using water-swellable polymers (hydrogels) which are themselves two-phase polymers and which exhibit a much wider range of swelling in water and organic solvents is described in U.S. Pat. Nos. 4,192,827 and 4,136,250.

In these hydrogel drug-carriers, the limited swelling ability of the hydrogels limits the amount of drug which can be imbibed into them from a drug solution, be it aqueous or organic in nature. If the polymer swells to a larger degree in a suitable organic solvent than in water, then higher drug-loadings can be achieved by loading from, for instance, ethanol/drug solutions than from aqueous solutions provided the drug is soluble in ethanol. The use of organic solvents to imbibe hydrogels with a drug for later release has also been described in U.S. Pat. No. 4,192,827.

Another hydrogel system for controlled release drug-delivery is described in U.S. Pat. No. 4,548,990.

This invention relates to controlled release, drug-delivery systems, and, more particularly, to a composition including a strongly swellable, moderately crosslinked polyvinylpyrrolidone (PVP) for effecting the desired controlled release of pharmaceutical medicaments.

2. Description of the Prior Art

PVP is widely used as a binding agent for pharmaceutical tablets. Normally, it is desired that the PVP binder itself not interference with the dissolution rate of the tablet in water, even after the product has experienced a considerable period of shelf-life. However, PVP is not ordinarily considered effective as a controlled release agent for drugs.

U.S. Pat. No. 5,073,614 describes the preparation of strongly swellable, moderately crosslinked PVP which can be made as fine white powders.

SUMMARY AND OBJECTS OF THE INVENTION

It is an object of this invention to provide a controlled-release, drug-delivery composition comprising an effective amount of a pharmaceutical medicament in a polymer substrate.

U.S. Pat. No. 4,548,990 describes a controlled-release, drug delivery composition comprising an effective amount of a pharmaceutical medicament in a polymer substrate which can swell in polar organic solvents to a much greater degree than conventional polymers used for drug-delivery and which therefore can be imbibed with active ingredients to a correspondingly high concentration while at the same time exhibiting only a moderate degree of swelling in water.

The ability of a polymer to absorb a large amount of water has always been considered a necessity for a polymeric orally used drug-delivery matrix. Hydrogels have therefore been the only materials previously used for this purpose. Drug diffusion through hydrophobic polymers is normally too slow to be of practical use in an oral drug-delivery. It is consistent with this explanation that hydrophobic polymer-medicament compositions have been used only as body implants where drug delivery over several weeks or even months is desired and where the overall dose size is very low, as is the case, for instance, with steroids.

It has now very unexpectedly been discovered that strongly swellable, moderately crosslinked PVP, as described in U.S. Pat. No. 5,073,614; can be used to provide an effective controlled-release, drug-delivery composition. The novel composition of the present invention comprises:

(A) a strongly swellable, moderately crosslinked PVP polymer in the form of fine, white powders having (a) an aqueous gel volume of about 15 to 150 ml/g of polymer, (b) a Brookfield viscosity in 5% aqueous solution of at least about 1,000 cps, which, (c) is prepared directly by precipitation polymerization of VP in the presence of about 0.1–1.5% of a crosslinking agent by weight of VP; and (B) an effective amount of a pharmaceutical medicament.

IN THE DRAWINGS

The FIGURE is a graphic representation of % drug released vs. time for various tablets containing PVP binders with different amounts of crosslinker, and a control of microcrystalline cellulose.

DETAILED DESCRIPTION OF THE INVENTION

In accordance with the invention, strongly swellable, moderately crosslinked PVP polymers are prepared directly in the form of fine, white powders by precipitation polymerization of vinylpyrrolidone in the presence of a predetermined amount of a crosslinking agent and free radical polymerization initiator in an organic solvent, preferably an aliphatic hydrocarbon, e.g. a $C_3$-$C_{10}$ saturated, branched or unbranched, cyclic or acyclic aliphatic hydrocarbon, and most preferably cyclohexane or heptane, or mixtures thereof.

The amount of solvent used in the process of the invention should be sufficient to dissolve an appreciable amount of the reactants and to maintain the copolymer precipitate in a stirrable state at the end of the polymerization. Generally, about 10 to 50% solids, preferably 15-30%, is maintained in the reaction mixture.

The precipitation polymerization process of the invention is carried out in the presence of a suitable free radical polymerization initiator. Suitable initiators include acyl peroxides such as diacetyl peroxide, dibenzoyl peroxide and dilauryl peroxide; peresters such as t-butylperoxy pivalate, tert-butyl peroxy-2-ethylhexanoate; peroxides such as di-tert-butyl peroxide; percarbonates such as dicyclohexyl peroxydicarbonate; and azo compounds such as 2,2'-azobis(isobutyronitrile), 2,2'-azobis(2,4-dimethylvaleronitrile), 1,1'-azobis(cyanocyclohexane), and 2,2'-azobis(methylbutyronitrile). Other initiators known in the art also may be used. A preferred initiator is the following:

| Preferred Initiator | | |
|---|---|---|
| t-Butyl peroxy-pivalate | Atochem N.A. (Lupersol 11) | Liquid: 75% active in mineral spirits |

The amount of such initiator may vary widely; generally about 0.1-1.5% is used, based on the weight of total monomers charged.

The reaction temperature may vary widely; generally the reaction mixture is maintained at about 40°-150° C., preferably 60°-70° C., during the polymerization. Pressure usually is kept at atmospheric pressure, although higher and lower pressures may be used as well.

The reaction mixture should be stirred vigorously under an inert atmosphere, e.g. nitrogen, during the polymerization. A stirring rate of about 100-600 rpm in a 1-liter lab reactor is quite adequate to effect the desired polymerization and to keep the precipitate in a stirrable state during the polymerization.

Suitable crosslinking agents for use in the invention include such multifunctional compounds as the divinyl ethers of an aliphatic diol, e.g. the divinyl ethers of 1,3-propanediol, 1,4-butanediol, 1,5-pentanediol, 1,6-hexanediol, 1,7-heptanediol, 1,8-octanediol, 1,9-nonanediol, 1,10-decanediol, 1,11-unidecanediol, and 1,12-dodecanediol; as well as the divinyl ethers of diethylene glycol, triethylene glycol, tetraethylene glycol, pentaethylene glycol, hexaethylene glycol, heptaethylene glycol, octaethylene glycol, nonaethylene glycol, decaethylene glycol and further polyalkylene glycols up to a molecular weight of about 6000. Other suitable crosslinking agents include 1,7-octadiene, 1,9-decadiene, 1,13-tetradecadiene, divinylbenzene, N-N'-divinylimidazolidone, and methylene bisacrylamide; acrylates such as polyethylene glycol diacrylate, trimethylolpropane triacrylate, propylene glycol diacrylate; allyl ether derivatives of polyhydric alcohols such as pentaerythritol triallyl ether or polyallyl sucrose; or polyhydric alcohols esterified once or twice with acrylic acid; triallylamine, tetraallylethylenediamine, diallyl phthalate, and the like. Preferred crosslinking agents are the following: N,N'-divinylimidazolidone, pentaerythritol triallyl ether, triallyl-1,3,5-triazine-2,4,6(1H,3H,5H)-trione and 2,4,6-triallyloxy-1,3,5-triazine.

The precipitation polymerization process of the invention may be carried out by first precharging a suitable reactor with a predetermined amount of the organic solvent, for example, an aliphatic hydrocarbon solvent, and heating the solvent to a desired reaction temperature while stirring vigorously under an inert gas atmosphere. The initiator is then charged into the reactor. Then a solution containing selected amounts of vinylpyrrolidone monomer and the crosslinker material is admitted into the reactor over a period of time, generally about an hour or more, and preferably below the surface of the solvent. Then the reaction mixture is held for an additional period of time for polymerization to be completed. Finally, the mixture is cooled to room temperature. Filtering, washing with solvent, and drying provides the desired polymer in yields approaching quantitative. Alternatively, the reaction product may be dried directly to provide the polymer powders.

The heterogeneous polymerization process of the invention in cyclohexane or heptane solvent provides the desired PVP polymer product as a fine, white powder, which precipitates readily, in quantitative yield, with substantially the same degree of crosslinking as the charge of VP monomer and crosslinking agent, in a smooth polymerization without excessive swelling of polymer during the course of the process. More particularly, the solvents of the invention are non-solvents for PVP and enable the polymerization to proceed in the presence of crosslinking agent without excessive building up viscosity of the reaction mixture during polymerization.

The invention will be illustrated by reference to the following examples, which are given in parts by weight unless otherwise specified.

EXAMPLE 1

A 2-liter, 4-necked reaction vessel was equipped with a condenser, a constant speed mechanical stirrer, set at 170 rpm with a torque indicator and an anchor agitator having an open radius of 4 and 5/6 inches, an adaptor for admitting nitrogen, and a thermocouple connected to a temperature controller. The vessel was charged with 1000 g. of cyclohexane and heated to 65° C. during 30 minutes while purging with nitrogen. The reactor then was held at 65° C. for an additional 30 minutes. Then 520 microliters of t-butylperoxy pivalate (Lupersol 11, 75% active) polymerization initiator was added. Thereafter a solution of 250 g. of vinylpyrrolidone and 1.25 g. of N,N'-divinylimidazolidone crosslinking agent was introduced into the charged reactor over a period of 4 hours while stirring the contents. The feeding rate was about 1.0 ml./min. Then the mixture was heated to 85° C. over a half-hour and held at that temperature for another half-hour. Then the mixture was transferred to a 2-liter high pressure reactor and 1.0 g. of 2,5-dimethyl-2,6-di-(t-butylperoxy)hexane (Lupersol 101, 90% active) was added. The reactor was sealed and heated to 130° C. for 8 hours, cooled to room temperature, and the mixture was dried in a rotary evaporator. The polymer product was oven dried at 100° C. and vacuum dried at 90° C. for 16 hours of each. A quantitative yield of a crosslinked PVP polymer containing about 0.5% crosslinking agent was obtained.

EXAMPLES 2-12

The procedure of Example 1 was followed using various amounts of different crosslinkers with the following results.

TABLE I

| Ex. No. | VP, (g) | Crosslinker* | Crosslinker, (g) | % Crosslinker |
|---|---|---|---|---|
| 1 | 250 | DI | 1.25 | 0.50 |
| 2 | 250 | DI | 0.25 | 0.10 |
| 3 | 250 | DI | 0.625 | 0.25 |
| 4 | 250 | DI | 2.5 | 1.00 |
| 5 | 250 | PETAE | 0.25 | 0.10 |
| 6 | 250 | PETAE | 0.5 | 0.20 |
| 7 | 250 | PETAE | 2.5 | 1.00 |
| 8 | 250 | MBA | 0.625 | 0.25 |
| 9 | 250 | MBA | 1.25 | 0.50 |
| 10 | 250 | MBA | 2.5 | 1.00 |
| 11 | 250 | DI | 5.0 | 2.00 |
| 12 | 250 | DI | 0.625 | 0.25 |

*DI = divinylimidazolidone
PETAE = pentaerythritol triallyl ether
MBA = methylene bisacrylamide

Properties of Polymer of Invention

1. Physical Properties

The strongly swellable, moderately crosslinked PVP polymer powders of the invention are characterized by its unique gel volume and viscosity, which properties enable the polymer to thicken aqueous and non-aqueous solutions effectively.

Gel volume is a measure of the swelling property of the crosslinked polymer and is defined as the equilibrium aqueous swelling volume of polymer per unit weight, and is expressed in the units of ml/g. Gel volume is determined by first adding 1 g. of the polymer to a suitable graduated cylinder filled with water. This mixture then is shaken and allowed to stand at room temperature for 3 days. The volume of the gel which is produced in water is measured and taken as the gel volume. Similarly, the gel volume concept can be applied to non-aqueous systems.

The viscosity of the polymer is defined by its Brookfield viscosity in cps, which is determined upon a 5% aqueous solution of the polymer at 25° C. by a standard analytical procedure using Model LTV and Spindle No. 4.

2. Controlled Release of Drugs

The effectiveness of the strongly swellable, lightly crosslinked PVP polymer in controlled release tablets was evaluated using theophylline as a model drug. Referring now to the FIGURE there is shown in graphical form the percentage of the drug in the sample tablet released with time when placed in water. The control is a sample tablet with microcrystalline cellulose present. The results show that slow release is achieved with strongly swellable, moderately crosslinked PVP over a crosslinking range therein in the amount of about 0.1 to 1%. At a 2% level, however, only a rapid release is obtained which is comparable to the poor results of the control.

The range of about 0.1-1% of the crosslinking agent in the PVP polymer provides effective controlled-release tablets containing the model drug theopylline which release about 6% of the drug hourly.

Preparation of a Drug-Containing Composition

The Active Ingredient (Drug)

Any of the drugs used to treat the body, both topical and systemic, can be incorporated as the active agent in the polymeric carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug. The desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided. For example, anabolics, e.g. methandrostenolone; analgesics, e.g. acetylsalicyclic acid, phenylbutazone or methadone; androgens, e.g. methyltestosterone; antibiotics, e.g. rifampin; antidepressants, e.g. imipramine or maprotiline; antidiabetics, e.g. phenformin; anticonvulsives, e.g. cabamazepine; antihistamines, e.g. tripelennamine; antihypertensives, e.g. hydralazine; antiinfectives, e.g. trimethoprim; antiparasitics, e.g. nifurimox; antiparkinson agents, e.g. levodopa; antiphlogistics, e.g. naproxen; antitussives, e.g. benzonstate; appetite depressants, e.g. mazindol; bronchodilators, e.g. fenoterol; coronary dilators, e.g. fenalcomine; corticoids, e.g. dexamethasone; cytostatics, e.g. floxuridine; diuretics, e.g. hydrochlorothiazide; hypnotics, e.g. glutethimide; neuroleptics, e.g. reserpine or thioridazine; psychoanaleptics, e.g. methylpenidate; tranquilizers, e.g. diazepan; uricosutics, e.g. sulfinpyrazone; vasodilators, e.g. isoproterenol.

Among the most preferred drugs are oxprenolol.HCl (TRASICOR) diclofenac-sodium (VOLTRAREN), baclofen (LIORESAL) metropolol.HCl (LOPRESSOR), beta blockers, such as oxprenolol and propanolol; calcium channel blockers, such as Nifedipine and Verapamil.

While the invention has been described with particular reference to certain embodiments thereof, it will be understood that changes and modifications may be made which are within the skill of the art. Accordingly, it is intended to be bound only by the following claims, in which:

What is claimed is:

1. A controlled-release, drug-delivery composition comprising:

(A) a strongly swellable, moderately crosslinked polymer consisting essentially of vinylpyrrolidone and a vinyl crosslinking agent in the form of fine, white powders characterized by (a) an aqueous gel volume of about 15 to 150 ml/g of polymer, and (b) a Brookfield viscosity in 5% aqueous solution of at least about 1,000 cps, which (c) is prepared directly by precipitation polymerization of vinylpyrrolidone in the presence of a vinyl crosslinking agent in the amount of about 0.1 to about 1% by weight of vinylpyrrolidone; and (B) an effective amount of a pharmaceutical medicament.

2. A composition according to claim 1 in which said vinyl crosslinking agent is selected from N,N'-divinylimidazolidone, pentaerythritol triallyl ether, triallyl-1,3,5-triazine-2,4,6(1H,3H,5H)-trione, polyallyl sucrose and 2,4,6-triallyloxy-1,3,5-triazine.

* * * * *